United States Patent [19]
Holmberg

[11] Patent Number: 5,429,625
[45] Date of Patent: Jul. 4, 1995

[54] TWO-PIECE OSTOMY APPLIANCE WITH POUCH-MOUNTED PRESSURE RING

[75] Inventor: Steen Holmberg, Marievej To, Denmark

[73] Assignee: Dansac A/S, Fredensborg, Denmark

[21] Appl. No.: 265,798

[22] Filed: Jun. 27, 1994

[51] Int. Cl.⁶ .................................... A61F 5/44
[52] U.S. Cl. .................................... 604/338
[58] Field of Search ...................... 604/338–342

[56] References Cited

U.S. PATENT DOCUMENTS

| | | | |
|---|---|---|---|
| 2,818,069 | 12/1957 | Fenton | 128/283 |
| 3,339,546 | 9/1967 | Chen | 128/156 |
| 3,385,298 | 5/1968 | Fenton | 128/283 |
| 4,219,023 | 8/1980 | Galindo | 128/283 |
| 4,419,100 | 12/1983 | Alexander | 604/339 |
| 4,477,325 | 10/1984 | Osburn | 204/159 |
| 4,578,065 | 3/1986 | Habib | 604/336 |
| 4,834,731 | 5/1989 | Nowak et al. | 604/339 |
| 4,973,323 | 11/1990 | Kaczmarek et al. | 604/339 |
| 5,125,917 | 6/1992 | Whealin | 604/340 |
| 5,185,008 | 2/1993 | Lavender | 604/338 |
| 5,316,607 | 5/1994 | Johnson et al. | 156/212 |
| 5,330,454 | 7/1994 | Klinger et al. | 604/338 |

FOREIGN PATENT DOCUMENTS 9205755 4/1992 WIPO .

*Primary Examiner*—Jerome L. Kruter
*Attorney, Agent, or Firm*—Tilton Fallon Lungmus

[57] ABSTRACT

A two-piece ostomy appliance in which the coupling ring of the pouch component is provided with a convex pressure ring element that forces the central portion of the faceplate component, within the opening of the faceplate coupling ring, into a similar convex configuration to cause stomal protrusion when the two components are coupled together and the appliance is worn.

10 Claims, 2 Drawing Sheets

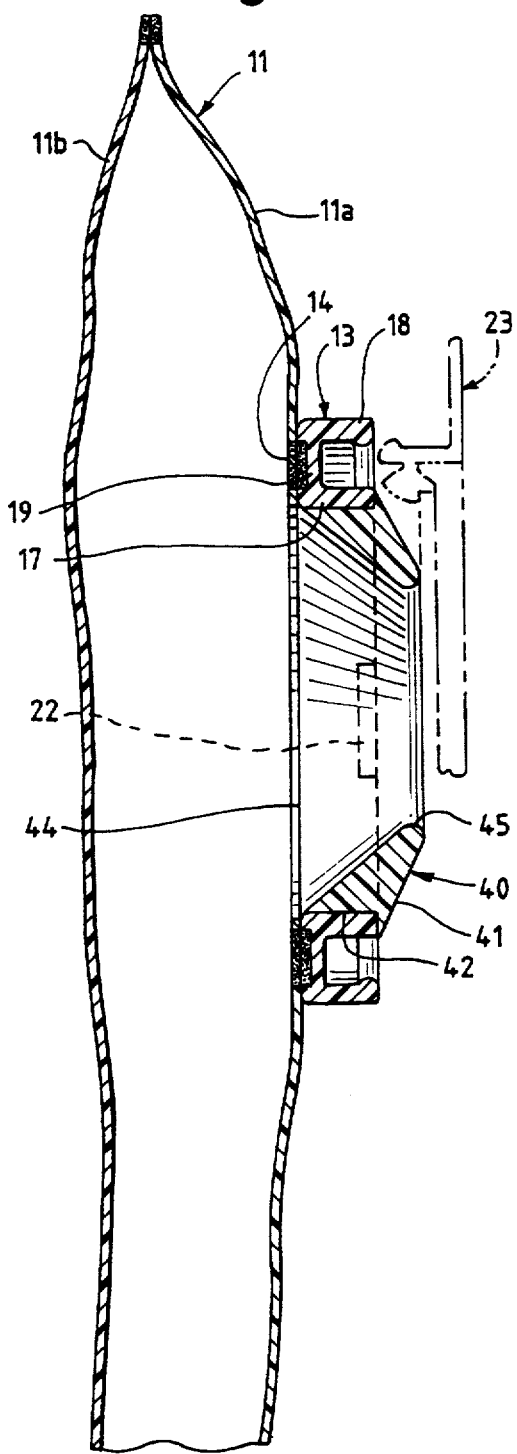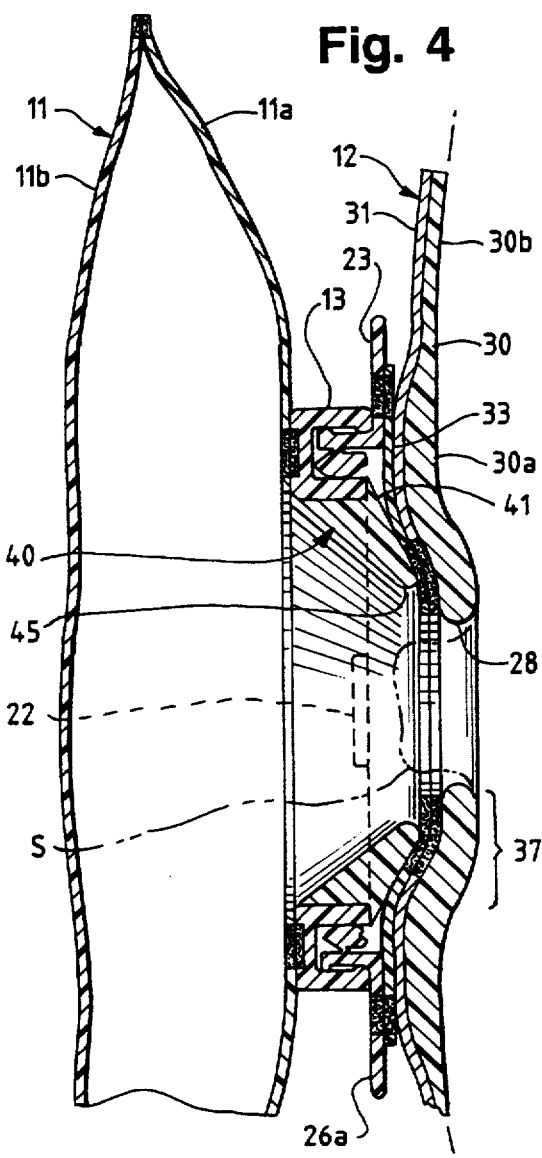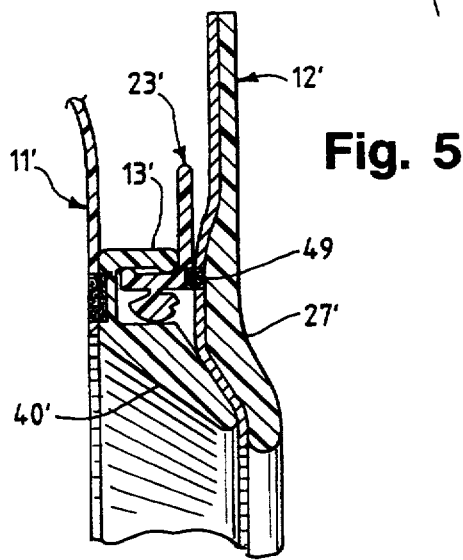

TWO-PIECE OSTOMY APPLIANCE WITH POUCH-MOUNTED PRESSURE RING

BACKGROUND AND SUMMARY

Ostomy patients with flush or recessed stomas have found that if external pressure is applied in the peristomal region, sufficient protrusion of the stoma may occur to aid in the discharge of effluent directly into the collection pouch, thereby prolonging the effectiveness of the adhesive seal between the faceplate and the peristomal skin surfaces. Some manufacturers of ostomy appliances have therefore provided relatively rigid convex annular inserts for use with the coupling rings of adhesive faceplates having skin barrier wafers attached thereto. In theory, such an insert is intended to deform the skin barrier wafer to increase peristomal pressure when the appliance is worn but, in practice, the insert usually lacks sufficient convexity to produce a significant change in the contour of the wafer. Inserts with greater convexity have been unavailable, presumably because of the excessive forces that would seem necessary, and the damage of faceplate coupling ring might sustain, in fitting such an insert into place. Also, to the extent that an insert having a convexity sufficient to depress the peristomal skin surfaces to a substantial extent would also encounter a reactionary force by reason of the resilience of the peristomal area sought to be depressed or deformed, an insert of greater convexity might actually reduce the effectiveness of the adhesive attachment between the faceplate and the skin. Such an effect would be especially noticeable when changing a pouch, since the forces applied to separate a pouch from the faceplate, added to the forces exerted by the skin against the convexity of the faceplace, may be more than enough to cause unintentional separation of the faceplate from the skin.

U.S. Pat. No. 4,834,731 discloses two-piece appliances (FIGS. 7-11) in which the faceplate components are provided with convex pressure rings by the manufacturer or are inserted by the user just prior to adhesive application of such a faceplate to the skin; in either case, such a pressure ring is secured to the proximal or body-side surface of the faceplate rather than being inserted through the faceplate coupling ring. While such a construction eliminates or reduces the aforementioned risks of coupling ring damage that might be Caused by insert attachment, it still requires stomal protrusion to occur at the time the faceplate is being adhesively applied to the skin surface with the result that the convexity of the pressure ring may make adhesive attachment of the faceplate more difficult. Other references indicating the state of the art are U.S. Pat. Nos. 4,973,323, 4,219,023, 3,385,298 and 2,818,069.

An important aspect of this invention therefore lies in providing a two-piece ostomy appliance in which the faceplate component may be adhesively attached to the peristomal skin surfaces prior to the application of deforming forces produced by a convex pressure ring. Unlike prior systems in which a pressure ring is part of a faceplate component, the system of this invention includes a convex pressure ring as either a permanent or detachable part of the pouch component of the two-piece assembly. Consequently, the forces causing stomal protrusion are not applied until after the faceplate component is already in place, thereby facilitating effective adhesive attachment of the faceplate component to the body. Furthermore, when a pouch is to be changed, there is little risk that the faceplate will also be unintentionally detached from the wearer because, unlike current two-piece systems in which a convex pressure ring is part of a faceplate and reactionary forces by the body against that ring may combine with the applied forces to produce unintentional faceplate removal, the convex pressure ring of this system acts as part of the pouch and, hence, the forces it exerts (and the reactionary forces exerted by the body) are removed (or relieved) along with removal of the pouch.

In a preferred embodiment, the faceplate component is of the "floating flange" type, meaning that the faceplate coupling ring is supported by a flexible web that permits a user to place his/her fingers between the faceplate coupling ring and the remainder of the faceplate at the time the faceplate ring is being joined to the mating ring of a pouch. Under such circumstances, the coupling operation aligns the convex pressure ring with that area of the faceplate against which pressure is to be applied, but substantial pressure causing protrusion of the stoma does not occur until after the components have been coupled together and a belt has been attached to the pouch ring and then tightened about the wearer's body. Subsequent tightening of the belt or strap therefore performs the dual functions of providing additional security to the attachment of the two coupling rings and of urging the convex pressure ring element into forceful contact with an annular portion of the flexible faceplate disposed within the opening of the faceplate ring to produce convex deformation of the faceplate and the desired extent of stomal protrusion.

The extent of stomal protrusion may be varied to some extent by adjusting the tightness of the belt. In addition, or alternatively, the extent of protrusion be varied by selecting a pouch component, or a pressure ring insert for a pouch component, that has the desired degree of convexity. In one embodiment of this invention, the convex pressure ring is a separate element that may be attached to and detached from a pouch coupling ring. Therefore, whether a convex pressure ring is to be used at all, and the selection of a convex pressure ring that produces the desired extent of stomal protrusion, are decisions that the wearer may make at the time the appliance is being applied.

The term "two-piece appliance" is used here in its usual sense to mean an appliance having separate pouch and faceplate components that are joined together at the time of use, in contrast to a one-piece appliance in which the pouch and faceplate are inseparable. Therefore, even though the pressure ring element used as part of this invention may itself be an element that is separable from the pouch coupling ring, and therefore constitutes an additional element, the appliance may still be properly regarded as a two-piece appliance.

Briefly, the appliance comprises a pouch having a pair of side walls, one of which is provided with a stoma-receiving opening and a first coupling ring secured to that wall about the opening. The faceplate is provided with a stoma-receiving aperture and has a bodyside surface provided with adhesive means, preferably in the form of a pliant, adhesive, moisture-absorbing skin barrier material, for adhesive attachment of the faceplate to a patient. The faceplate also includes a pouchside surface with a second coupling ring connected thereto for mating engagement with the first coupling ring of the pouch. The faceplate's second coupling ring extends about the stoma-receiving aperture and has an opening substantially larger than that aperture to expose a flexible and deflectable annular portion of the faceplate within that opening. Pressure ring means are provided by the first coupling ring (i.e., the pouch coupling ring) and is extendable into the opening of the second coupling ring for engaging the annular portion of the faceplate and forcing that portion in a bodyside direction when the rings are coupled together and the faceplate is worn.

Other features, advantages, and objects of the invention will become apparent from the specification and drawings.

DRAWINGS

FIG. 3 is a perspective view showing the pouch component of FIGS. 1 and 2 with the convex pressure ring element attached to the pouch coupling ring.

FIG. 4 is a sectional view showing the components in assembled condition as the appliance would be worn by a patient.

FIG. 5 is a fragmentary sectional view of a second embodiment in which the convex pressure ring element is formed integrally with the pouch coupling ring.

Detailed Description of Preferred Embodiments

Figure 1:
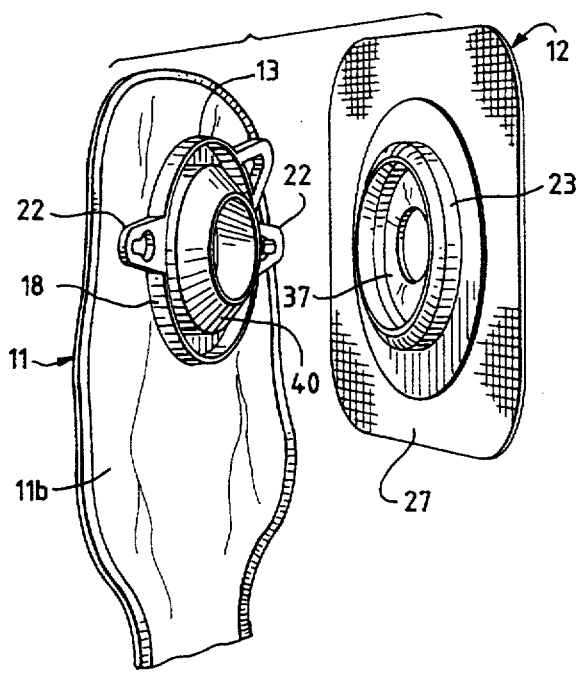
FIG. 1 is a perspective view of a two-piece ostomy appliance embodying this invention, the pouch and faceplate components being shown in separated condition for clarity of illustration.

Referring to FIGS. 1-4, the numeral 10 generally designates a two-piece ostomy appliance essentially composed of a pouch component 11, having side walls 11a and 11b, and a faceplate component 12. The two components are provided with coupling rings that are detachably connected at the time of use for securely joining and sealing the parts together. Thus, the pouch component 11 includes a first coupling ring 13 secured by annular heat seal 14 to bodyside wall 11a about an opening 16 in that wall. Coupling ring 13 is channel-shaped in cross section, having a pair of inner and outer side walls 17 and 18 joined by a connecting wall 19. An annular channel 20 faces in an axial (bodyside) direction away from the pouch. The coupling ring 13 has a large stoma-receiving opening 21, and a pair of laterally-projecting, diametrically-disposed, integral ear portions or tabs 22 project from outer side wall 18 as shown most clearly in FIG. 1. The ears are apertured for connection to a conventional support belt (not shown) in a manner well known in the art.

Similarly, the faceplate component 12 is provided with a second coupling ring 23 having a bulbous wedge portion 24 supported by annular stem 25 from annular collar portion 26. The faceplate coupling ring also includes a radially-extending flange portion 26a.

The coupling rings shown in the drawings are essentially the same in construction and operation as disclosed in co-owned U.S. Pat. No. 5,185,008, the disclosure of which is incorporated by reference herein. While coupling rings of such construction are believed particularly advantageous for the reasons disclosed in that patent, coupling rings of different constructions are also well known in the art and may be utilized here. In all of such constructions, the coupling rings are typically formed of flexible, resilient plastic materials such as polyethylene and are capable of being coupled together mechanically, adhesively, or both.

Figure 2:
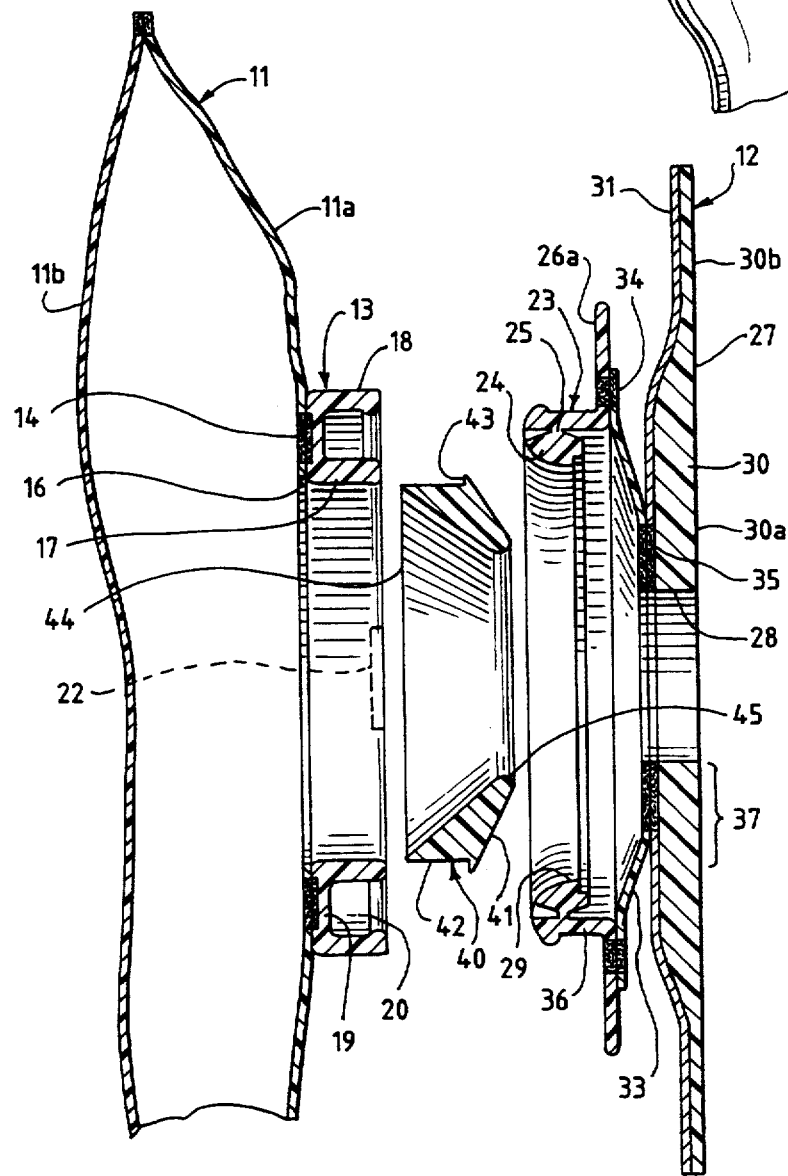
FIG. 2 is an enlarged fragmentary vertical perspective view showing the components in separated condition with the convex pressure ring element detached from the pouch coupling ring.

Faceplate component 12 also includes an adhesive attachment plate 27 for securing the faceplate component to a wearer. The plate includes a central stoma-receiving aperture 28 extending therethrough and coaxial with the relatively large opening 29 of faceplate coupling ring 23. The attachment plate is composed of a bodyside adhesive layer 30 and a pouchside microporous non-woven layer 31. Ideally, the adhesive layer is composed of a swellable, water-absorbing, hydrocolloid-containing adhesive skin barrier material having both wet and dry tack. Such material should also be pliant and readily deformable. A variety of so-called skin barrier materials having such properties are well known in the art and may be used here. Examples of adhesive skin barrier compositions are found in U.S. Pat. Nos. 4,477,325, 4,578,065 and 3,339,546. While the use of skin barrier materials in the appliance of this invention is preferred, it is to be understood that other flexible, pressure-sensitive adhesive materials, such as medical-grade acrylic adhesives of the type commonly used with microporous tapes, may instead be utilized here.

Where the adhesive material is of the moisture-absorbing skin barrier type, layer 30 is preferably contoured as shown most clearly in FIGS. 2 and 4. The annular inner body portion 30a is relatively thick, having a thickness well in excess of 0.5 mm, whereas the outer flange portion 30b is wide and relatively thin. Specifically, the flange portion should have a radial width of 5 mm or more but should have a substantially uniform thickness not exceeding about 0.5 mm. The advantages of such a contouring of the adhesive layer are brought out in International Publication WO 92/05755, published Apr. 16, 1992, based on application PCT/US91/06665. Such contouring has been found particularly desirable for avoiding problems of channeling and leakage while at the same time providing a faceplate having a relatively high capacity for absorbing perspiration and stomal fluids without losing its capacity for adhesive attachment to the skin.

Faceplate coupling ring 23 may be secured directly to the microporous layer 31 of plate 27 but, in the embodiment depicted in FIGS. 1-4, the coupling ring is attached to the remainder of the faceplate by means of a thin flexible web 33 that extends radially inwardly from the ring, such web being secured along its outer margin to flange portion 24 by means of heat seal 34 and along its inner margin to layer 31 of plate 27 by heat seal 35 which immediately surrounds aperture 28. The annular web 33 allows limited axial movement of faceplate coupling ring 23 with respect to plate 27. Such limited floating action permits a user to insert his/her fingers behind faceplate coupling ring 23 when that ring is being mated with pouch coupling ring 13, thereby avoiding pressure that might otherwise be exerted against the abdomen during a pouch-faceplate coupling operation. For further discussion of the structure and advantages of such a floating flange construction, reference may be had to co-owned U.S. Pat. No. 4,419,100, 4,213,358 and 5,185,008.

Aperture 28 may be enlarged with scissors by a user so that it conforms generally with, and is slightly larger than, the stoma. Even if so enlarged, aperture 28 will remain substantially smaller in size than the opening 29 defined by faceplate coupling ring 23. Opening 28 will also remain considerably smaller khan opening 21 of pouch coupling ring 13. Consequently, an annular zone 37 (FIG. 2) of flexible attachment plate 27 extends radially inwardly for a substantial distance from the innermost limits of coupling rings 13 and 23. That zone 37 provides a contact area for a convex pressure ring element 40 provided by the pouch coupling ring 13 (FIGS. 1, 4).

As shown most clearly in FIG. 2, the pressure ring element 40 has a convex or frusto-conical front face 41, a generally cylindrical outer surface 42, and a rearwardly-facing shoulder 43 therebetween. The passage through the convex pressure ring is also frusto-conical, defining a relatively large opening 44 at the rear end of the ring (preferably of a size identical to that of opening 21 of pouch coupling ring 13) and a relatively small front opening 45 defined by rounded bearing surfaces at the front of the pressure ring. It will be noted that opening 45, while substantially smaller than opening 44, is nevertheless significantly larger than aperture 28 of faceplate 12.

In the embodiment depicted in FIGS. 1–4, the pressure ring is formed as a separate insert element to be snugly received in opening 21 of pouch coupling ring 13. The generally cylindrical outer surface 42 of the insert element is of substantially the same size as opening 21. Shoulder 43 serves as a stop to limit the extent of insertion of the pressure ring into pouch coupling ring 13 and, in addition, functions as an extension of convex surface 41 leading into the annular channel 20 of the pouch coupling ring when that ring and the pressure ring are assembled.

Pressure ring 40 is relatively rigid because of its material, mass, and configuration. The term "relatively rigid" is here used to mean that the pressure ring retains its shape under normal conditions of use. While various materials may be used, rigid or semi-rigid plastics, such as polypropylene, polyethylene, or polystyrene are considered particularly suitable.

The slope and axial extent of front face 41 may be varied depending on peristomal pressure required to cause protrusion of a stoma. Pressure ring inserts may be provided with front faces of different angles within the range of about 10 to 60 or more degrees, the slope being measured as the included angle between the frusto-conical surface and a plane normal to the axis of the pressure ring. A set of such pressure rings of different angles may be provided from which a user may select the ring most suitable for his/her particular requirements.

It will be noted that the axial dimension of the convex pressure ring 40 greatly exceeds the corresponding dimension of faceplate coupling ring 23 so that the convex face 41 protrudes forwardly (in a bodyside direction) well beyond flange 26a of coupling ring 23 when the parts are assembled and coupled together as depicted in FIG. 4. When a belt attached to the ears 22 of pouch ring 13 is tightened, the pouch ring is drawn towards the wearer's body and the pressure ring 40 carried or provided by the pouch ring is urged into forceful contact with faceplate 12 to reform the annular portion or zone 37 of the attachment plate 27 into the convex configuration illustrated in FIG. 4. Stoma S, depicted in broken lines in that figure, is therefore caused to protrude into aperture 28 and, preferably, into the outwardly-flared passage of the pressure ring 40.

In the embodiment of FIG. 5, the pouch coupling ring 13' and convex pressure ring 40' are formed integrally rather than as separate components. In other respects, the pouch and pressure ring assemblies of the two embodiments are identical. However, there is a further difference with respect to the faceplate components 12, 12' of the two embodiments. In FIG. 5, faceplate coupling ring 23' is shown as being secured directly to attachment plate 27' by heat seal 49, thereby eliminating the web 33 of the first embodiment. It is to be understood that the embodiment of FIG. 5 may, of course, be provided with such a web (in which case the faceplate component of FIG. 5 would be identical to that shown in FIGS. 1–4) and, conversely, that the web 33 of the embodiment of FIGS. 1–4 might be omitted (in which case the faceplate component of that embodiment would be identical to the one depicted in FIG. 5).

While in the foregoing, embodiments of the invention have been disclosed in considerable detail for purposes of illustration, it will be understood by those skilled in the art that many of those details may be varied without departing from the spirit and scope of the invention.

What is claimed is:

1. A two-piece ostomy appliance comprising a pouch and a flexible faceplate; said pouch having a pair of side walls, one of which is provided with a stoma-receiving opening, and a first coupling ring secured to said one wall about said opening; said faceplate having an aperture and having a bodyside surface provided with adhesive means for adhesive attachment of the faceplate to a patient; said faceplate also having a pouchside surface with a second coupling ring connected thereto for mating engagement with said first coupling ring; said second coupling ring extending about said aperture and having an opening substantially larger than said aperture to expose a flexible and deflectable annular portion of said faceplate within the opening of said second coupling ring, wherein the improvement comprises inclusive said first coupling ring having pressure ring means and extendable into the opening of said second coupling ring for releasably engaging the pouchside surface of said exposed flexible annular portion of said faceplate and forcing the same in a bodyside direction when said coupling rings are coupled together and said appliance is worn.

2. The appliance of claim 1 in which said pressure ring means comprises an integral extension of said first coupling ring.

3. The appliance of claim 1 in which said pressure ring means comprises a separable component detachably connected to said first coupling ring.

4. The appliance of claim 3 in which said pressure ring means comprises a relatively rigid pressure ring having a convex front face extending beyond said first coupling ring when said pressure ring and said first ring are connected together.

5. The appliance of claim 4 in which said pressure ring has a frusto-conical inside surface.

6. The appliance of claim 4 in which said pressure ring has a generally cylindrical outer surface having an opening of substantially the same size as said opening of said first coupling ring.

7. The appliance of claim 6 in which a portion of said pressure ring having said cylindrical surface is insertable into said opening of said first coupling ring; said pressure ring also having stop means for limiting the extent of such insertion.

8. The appliance of claim 7 in which said stop means comprises a shoulder provided by said pressure ring and extending radially outwardly between said cylindrical surface and said front face.

9. The appliance of claims 2 or 3 in which said pressure ring means extends through the opening of said second coupling ring, and a substantial distance beyond said second coupling ring, when said pouch and faceplate are coupled together.

10. The appliance of claims 2 or 3 in which said pressure ring means has a convex front face extending through and beyond the opening of said second coupling ring when said first and second coupling rings are coupled together; said pressure ring means having a rounded front edge defining an opening substantially larger than said aperture of said faceplate but smaller than said opening of said second coupling ring.

* * * * *